(12) United States Patent
Ohzu et al.

(10) Patent No.: US 7,117,101 B2
(45) Date of Patent: Oct. 3, 2006

(54) REMOTE PARTICLE COUNTER FOR REMOTE MEASUREMENT OF THE NUMBER AND SIZE DISTRIBUTION OF SUSPENDED FINE PARTICLES IN THE ATMOSPHERE

(75) Inventors: Akira Ohzu, Ibaraki (JP); Masaaki Kato, Ibaraki (JP); Katsuaki Akaoka, Ibaraki (JP); Yoichiro Maruyama, Ibaraki (JP)

(73) Assignee: Japan Atomic Energy Research Institute, Kashiwa (JP)

( * ) Notice: Subject to any disclaimer, the term of this patent is extended or adjusted under 35 U.S.C. 154(b) by 94 days.

(21) Appl. No.: 10/764,567

(22) Filed: Jan. 27, 2004

(65) Prior Publication Data

US 2004/0184025 A1    Sep. 23, 2004

(30) Foreign Application Priority Data

Jan. 28, 2003    (JP)    ............................. 2003/018787

(51) Int. Cl.
*G06F 13/10*    (2006.01)
(52) U.S. Cl. ........................ 702/29; 702/128; 702/149; 702/150

(58) Field of Classification Search ............ 702/23–26, 702/66, 69, 183, 188, 189, 128, 149, 150, 702/182; 242/54; 256/4.01; 701/59; 250/559.38
See application file for complete search history.

(56) References Cited

U.S. PATENT DOCUMENTS

| 5,298,905 | A | * | 3/1994 | Dahl ............................ 342/54 |
| 5,394,238 | A | * | 2/1995 | Mocker et al. ............. 356/342 |
| 6,066,295 | A | * | 5/2000 | Bernstein et al. ............. 422/50 |
| 6,490,530 | B1 | * | 12/2002 | Wyatt ........................... 702/24 |
| 2002/0118352 | A1 | | 8/2002 | Ohzu et al. |

* cited by examiner

*Primary Examiner*—Marc S. Hoff
*Assistant Examiner*—Felix Suarez
(74) *Attorney, Agent, or Firm*—Banner & Witcoff, Ltd.

(57) ABSTRACT

A remote particle counter comprising a pulsed laser generator, laser light emitting optics, scattered light collecting optics, a high-sensitivity two-dimensional photo detector as a scattered light detecting portion having a fast gating capability such as a CCD camera, and a control and measure system, wherein suspended fine particles forming aerosols in the atmosphere which are far away from the site of laser emission are illuminated with laser light, the resulting backward scattered light from the individual fine particles is detected as image, and the number and size distribution of the suspended fine particles are measured at a remote site.

4 Claims, 3 Drawing Sheets

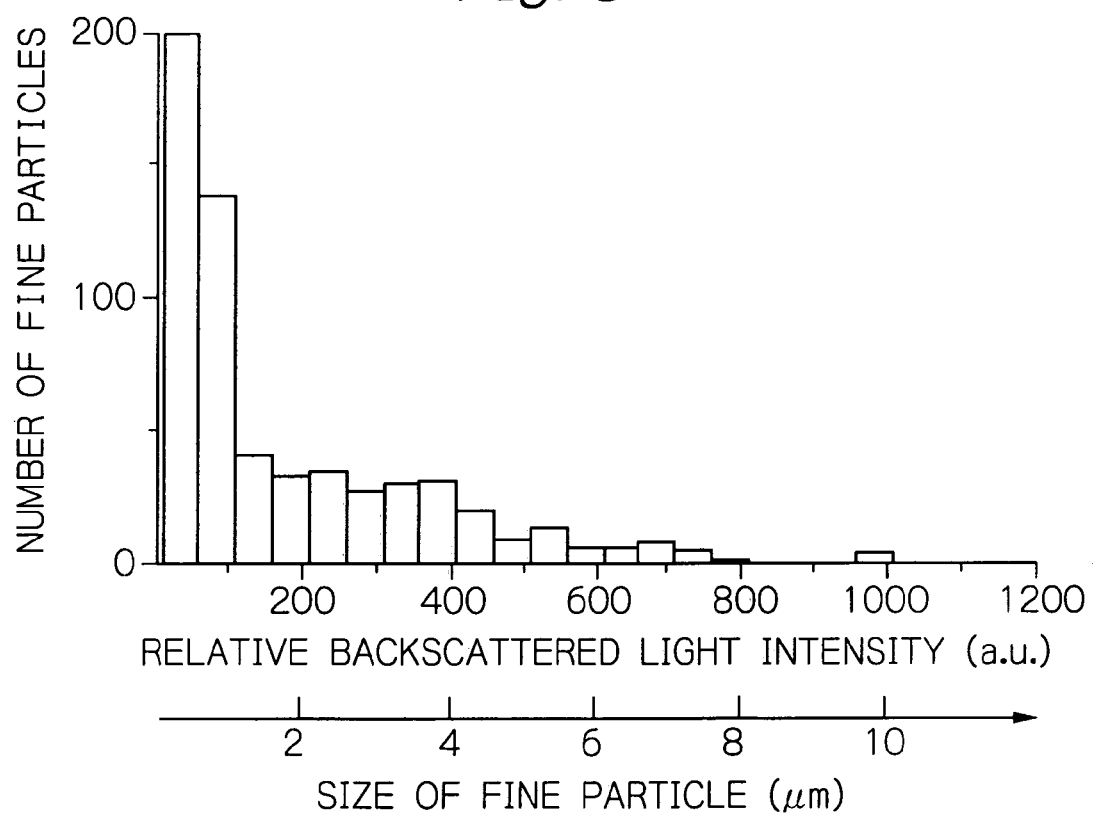

REMOTE PARTICLE COUNTER FOR REMOTE MEASUREMENT OF THE NUMBER AND SIZE DISTRIBUTION OF SUSPENDED FINE PARTICLES IN THE ATMOSPHERE

This application is based upon and claims the benefit of priority from Japanese Patent Application No. 18787/2003 filed Jan. 28, 2003, the entire contents of this application are incorporated herein by reference.

BACKGROUND OF THE INVENTION

This invention is applicable to fields where a laser radar or other device is used to measure atmospheric fine particles, particularly to the industry of atmospheric environmental analysis where atmospheric aerosols and fine particles are observed or detected. The invention is also applicable to meteorological industries and academics where there are needs to monitor and study harmful environmental pollutants such as SPM (suspended particulate matter) and diesel dust that are released and suspended in the atmosphere due, partly to natural phenomena, and partly to various industrial activities and transportation vehicles, as well as scattering volcanic ashes and cedar pollens.

The prior art offers a technology by which two pieces of information about atmospheric fine particles, i.e., their number and size distribution, are determined directly or indirectly using a particle counter (e.g. of a desktop laser scattering type) or an impactor placed on the ground and within a room (see, for example, JIS B9921 1989 "Automatic Particle Counter of Light Scattering Type"; "Handbook of Laser Measurement", ed. by the Editorial Committee of Laser Measurement Handbook, p. 229–234, 1993; "Latest References for Optical Sensing Technology", Kazuo Ichijo, Optronics Inc., p. 90–91, 2001; and Japanese Patent Public Disclosure Hei 8-86737). However, it is impossible for those devices to measure directly the number and size distribution of fine particles in the atmosphere either several hundred meters above the ground or several kilometers away from the site of observation. Direct measurement would be possible if the devices were installed in that above-ground or faraway atmosphere but this is not realistic.

The conventional laser radar system is capable of obtaining the information about the fine particles in the faraway atmosphere (see, for example, "Latest References for Optical Sensing Technology—Visualizing the Earth's Atmospheric Environment by Optical Remote Sensing", Nobuo Sugimoto, Optronics Inc., p. 270–275, 2001; "Handbook of Spectroscopic Technology—Laser Remote Sensing", ed. by Shigeo Minami and Yoichi Goshi, Asakura Shobo, p. 581–591, 1990; and Japanese Patent Public Disclosure 2001-337029) but even that system cannot directly measure the number and size distribution of atmospheric fine particles since what it does is simply sum the intensities of scattered light from the individual fine particles in the atmosphere and measure a single signal intensity.

The operating principle of the desktop particle counter in the prior art is such that the air continuously drawn into the device is illuminated with laser light or the like and the scattered light beams from the fine particles in the air are counted one by one. By this approach, the number and size distribution of fine particles in a unit volume of air can be measured but not if the air is the atmosphere high above the ground. The information about faraway fine particles can be measured by the laser radar system; however, in the conventional laser radar system, it is impossible to measure the scattered light beams from individual particles in the faraway atmosphere and directly calculate the number and size distribution of the fine particles contained within a limited space. In order to make this calculation possible, the fine particles within a faraway limited space in the atmosphere must be illuminated with laser light and the scattered light beams from the fine particles be detected one by one.

SUMMARY OF THE INVENTION

According to the present invention, the method of emitting laser light in the conventional laser radar system and the method of receiving the scattered light from fine particles in the atmosphere are modified such that the number and size distribution of the fine particles can be measured simultaneously. The first step in the process of the invention is emit pulsed laser light into the atmosphere with a certain angle of divergence.

The pulsed laser light emission spreads as it propagates through the atmosphere and hits fine particles in the atmosphere, whereupon it is scattered. Backward scattered light that travels in a direction opposite to the direction of laser light propagation is measured with a high-sensitivity two-dimensional photo detector such as a CCD camera device having a fast gating capability, whereupon the individual fine particles in the atmosphere are captured as image. The image is then analyzed to determine the number and size distribution of the fine particles contained within a limited faraway space in the atmosphere.

BRIEF DESCRIPTION OF THE DRAWINGS

FIG. 3 is a histogram showing the size distribution of fine particles in the atmosphere as constructed by analyzing the number and brightness of spots of scattered light from the fine particles on the basis of the image data shown in FIG. 2.

DETAILED DESCRIPTION OF THE INVENTION

Pulsed laser light is emitted into the atmosphere as it is spread such that the scattered light from the population of atmospheric fine particles to be measured is confined within a two-dimensional light detecting portion of scattered light collecting optics. During the propagation of the laser light, backward scattered light occurs from the population of fine particles contained in a broad range of the atmosphere. The backward scattered light occurring from the fine particles in a direction opposite the direction of laser light propagation is observed from a site near the point of laser emission through a light collecting element such as a telescope by means of a two-dimensional detector such as a CCD camera or MCR (micro-channel plate) that have a fast gating capability.

Since the two-dimensional photo detector has a fast gating capability, by controlling the shutter timing as functions of the shutter time of the two-dimensional light detecting element and the delay time from laser emission, the backward scattered light from the individual atmospheric fine particles at any distance from the site of observation can be measured as image. The image looks like either a dense or sparse cloud of spots. Since the number and brightness (scattered light intensity) of the spots represent the number and size distribution, respectively, of the fine particles contained in the space of interest illuminated with pulsed laser light, the two parameters may be counted to measure the number and size distribution of the fine particles suspended in any limited space of the atmosphere.

Figure 1:
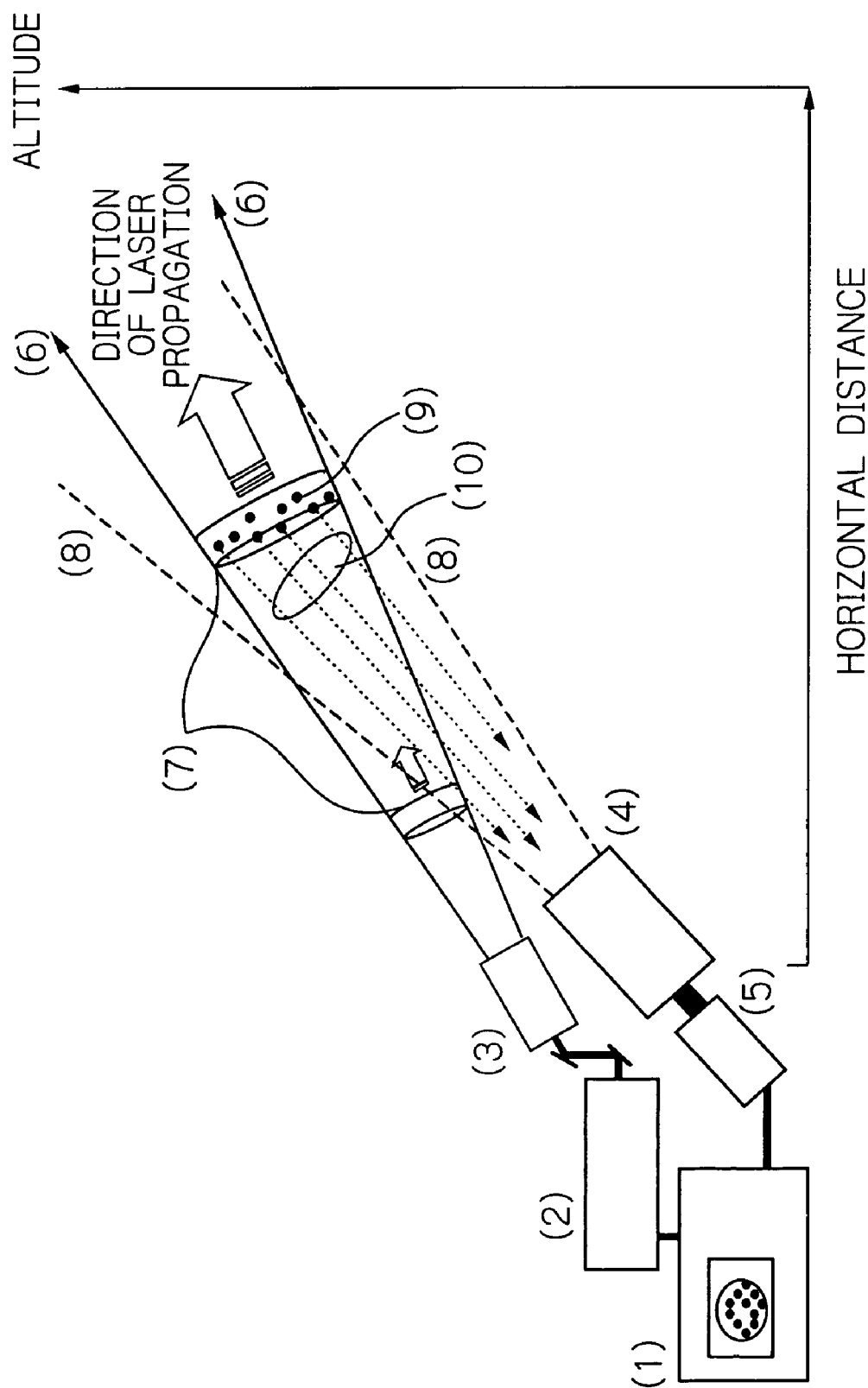
FIG. 1 is a schematic of a remote particle counter system embodying the method of the invention.

FIG. 1 is a schematic of a remote particle counter system embodying the method of the invention. The system is composed of a control/analysis section 1 that not only performs overall control of the system but also data measurement and analysis, a pulsed laser generator 2, laser beam emitting optics 3 for transmitting a spread beam of laser light toward the atmosphere, scattered light collecting optics 4 by which backward scattered light 10 that occurred from fine particles upon illumination with laser light is collected on a detector, and a high-sensitivity two-dimensional photo detector 5 having a fast gating capability. The scattered light collecting optics 4 has a field of view indicated by dashed lines 8.

Indicated by 9 is a population of fine particles that were released either from industrial plants or by the natural process and suspended over a certain area of the atmosphere at a certain altitude. This target area is illuminated with pulsed laser light 7 of a wide beam spread that has been emitted from the laser generator 2 controlled by the control/analysis system 1 and which has passed through the laser beam emitting optics 3. Backward scattered light 10 occurs from the distributed atmospheric fine particles and is collected by the scattered light collecting optics 4 to be picked up by the high-sensitivity two-dimensional photo detector 5, which is controlled by the control/analysis system 1 to measure the number and size distribution of the fine particles 9. The direction of laser emission is indicated by 6 and by controlling this direction and the delay time from laser emission of the fast gating of the high-sensitivity two-dimensional photo detector 5, the spatial distribution in the atmosphere of the number and size distribution of the fine particles is obtained. In addition, by observing the temporal variations of that spatial distribution in the atmosphere, one can obtain data on the wind direction and velocity for the atmosphere.

Figure 2:
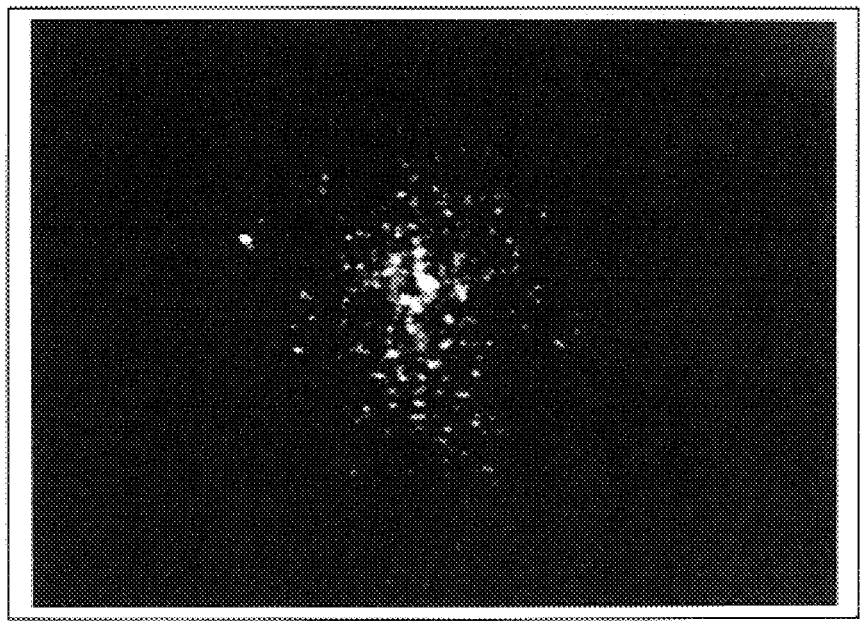
FIG. 2 is a micrograph showing the observation data captured with a high-sensitivity CCD camera equipped with an image intensifier having a fast gating capability.

FIG. 2 is a micrograph showing the observation data captured with a high-sensitivity CCD camera equipped with an image intensifier having a fast gating capability. A YAG laser light beam having a diameter of about 1 cm (wavelength, 532 nm; pulse width, 1 ns; pulse energy, 30 mJ) was emitted into the atmosphere at an angle of about 20 degrees from the horizontal, with the half viewing angle being about 1 degree, and the backward scattered light returning from the target atmospheric fine particles about 100 m away was measured with the CCD camera. The gate width (shutter time) was about 3 ns. The clear spots in FIG. 2 represent the scattered light from the population of fine particles suspended in a cylindrical space about 3 m in diameter and about 1 m long which was assumed 100 m away from the position of laser emission. By measuring the number and brightness of those clear spots, one can determine the number and size distribution of the fine particles suspended in the target space of the atmosphere.

FIG. 3 is a histogram showing the size distribution of fine particles in the atmosphere as constructed by analyzing the number and brightness of spots of scattered light from the individual fine particles on the basis of the image data shown in FIG. 2. The brightness of scattered light is assumed to be substantially proportional to the size of the particle from which it has been scattered. The largest fine particle suspended in the atmosphere is typically about 10 µm in diameter. Considering these, the axis for particle size which extends horizontally under the scale of relative backward scattered light intensity can be fitted. By employing the present invention, a histogram data for the size distribution of fine particles that is similar to the one obtained with a desktop particle counter typically used on the ground can be obtained for the heretofore inaccessible faraway atmospheric fine particles from a remote site (on the ground).

The invention is described below on the basis of field measurement and experimental data.

EXAMPLE 1

Field Measurement

FIG. 1 is a schematic of a laser-radar based remote particle counter system embodying the method of the invention. The system is composed of a pulsed laser generator 2, laser beam emitting optics 3 for transmitting a spread beam of laser light toward the atmosphere, collecting optics 4 by which backward scattered light coming a long distance from the atmosphere is collected on a high-sensitivity two-dimensional photo detector 5 having a fast gate sweeping capability, and a control/analysis section 1 that performs not only overall control of the system but also analysis of the data obtained by the detector 5.

First, a spread beam spot of pulsed laser light 7 was issued from the laser 2 toward the area of the atmosphere to be observed. After emerging from the optics 3, the pulsed laser light 7 progressively increased its beam spot diameter as it propagated through the atmosphere in a near cylindrical shape having a length comparable to the laser pulse duration.

As shown, backscattered light 10 was issued from the population of fine particles suspended in the spatial area of the atmosphere through which the pulsed laser light 7 was passing. The direction of the backscattered light 10 was opposite to the direction of laser propagation indicated by 6. As laser light propagated, backscattered light 10 occurred successively from all the fine particles existing in the atmospheric area through which the laser light was propagating. The backscattered light 10 was collected by the optics 10 typically in the form of a telescope and thereafter detected as an image on the screen of the high-sensitivity two-dimensional photo detector having a fast gating capability (as exemplified by a high-speed, high-sensitivity MCP combined with a CCD device).

If the gate (shutter) of the two-dimensional photo detector 5 is open, not only the scattered light from near-distance fine particles but also the scattered light from faraway fine particles are successively collected as the laser light propagates and one cannot tell which scattered light (hence which image) came from which space (as containing fine particles). To deal with this problem, the fast gating capability of the two-dimensional photo detector 5 is activated and the scattered light it is collecting is sequentially chopped by the shutter action of the high-speed gate (of a short time duration), whereupon as shown in FIG. 1, only the backward scattered light coming from the population of fine particles within a specific area of the range of laser propagation can be selectively picked up as an image.

Further, if the shutter timing is delayed a certain time from the emission time of pulsed laser light, only the scattered light from the population of fine particles present in a limited space of the range of laser propagation a specified distance away from the site of laser emission can be captured as an image (see FIG. 1). The captured image is either a dense or sparse cloud of spots as shown in FIG. 2. To state specifically, if the shutter of the two-dimensional photo detector 5 is opened and closed at short time intervals with a certain delay time from the emission time of pulsed laser light 7 from the pulsed laser generator 2, only the backscattered light from the population of fine particles in a space far away from the site of laser emission in the direction of travel of the pulsed laser light can be detected as shown in FIG. 2.

EXAMPLE 2

Experimental Data

FIG. 2 is a micrograph showing the observation data captured with a CCD camera equipped with an image intensifier which was used as the high-sensitivity two-dimensional photo detector having a fast gating capability in the measuring setup described in Example 1. A YAG laser light beam having a diameter of about 1 cm (wavelength, 532 nm; pulse width, 1 ns; pulse energy, 30 mJ) was emitted into the atmosphere at a wide angle, with the half viewing angle being about 1 degree, and the backward scattered light returning from the target atmospheric fine particles about 100 m away was measured with the CCD camera. The gate width (shutter time) was about 3 ns.

The clear spots in FIG. 2 represent the scattered light from the population of fine particles suspended in a cylindrical space about 3 m in diameter and about 1 m long which was assumed 100 m away from the position of laser emission. Since the number and brightness of those clear spots represent the number and size, respectively, of the fine particles, one may analyze them to determine the size distribution of the fine particles as shown in FIG. 3.

The intensity of the laser light applied to fine particles and the intensity of the light scattered from them are related by the following equation (1). As can be seen from eq. (1), if observations are made at the same site and if the fine particles are of the same shape (spherical) and homogeneous, the brightness of a spot on image represents the intensity of scattered light, so the particle size can be reasonably assumed from the scattered light intensity. Therefore, by analyzing the brightness and number of the spots, one can derive the size distribution of the fine particles as shown in FIG. 3. If the highest value of relative scattered light intensity is assumed to derive from particles having a size of about 10 μm and if it is also assumed that the scattered light intensity is substantially proportional to the particle size, a scale of particle size can be set under the axis of relative scattered light intensity. By this procedure, one can determine the number, density and size distribution of faraway fine particles in the atmosphere:

$$I_s = \int_{wc} I_i \cdot F(\theta, \phi, a, m)/(kr)^2 dw \quad (1)$$

$$\alpha = \pi Dp/\lambda, k = 2\pi/\lambda$$

where in the case of perfectly spherical particles,
$I_s$: the intensity of scattered laser light from fine particles
$I_i$: the intensity of issued laser light
$\lambda$: laser wavelength
$D_p$: the size of a fine particle
m : the refractive index of a fine particle relative to air
ωc: light collecting solid angle
r: the distance from a fine particle to the observation site F: the scattering function of a fine particle
θ: the horizontal angular difference between the axis parallel to the direction of scattered light and the axis parallel to the direction of laser propagation;
ψ: the vertical angular difference between the axis parallel to the direction of scattered light and the axis parallel to the direction of laser propagation (Tadasu Suda and Kazuya Tsukada, "Laser-Based Fine Particle Measuring Technology", in Sensor Technology, 7, 2 (1987)).

According to the invention, the number and size distribution of faraway suspended fine particles in the atmosphere which have heretofore been inaccessible by the prior art can be measured and the spatial distribution of such particles can be measured real-time and precisely over a broad area. Therefore, information about the smoke of a volcano, as well as information about air pollution by environmental pollutants or environmental pollution by automotive exhaust gas can be obtained real-time and accurately.

If the measured data are incorporated into relevant environmental programs, they can contribute to the protection and preservation of the environment. If the present invention is applied to an unexpected trouble such as leakage of a harmful substance from a plant facility, residents around the facility and passersby can be kept informed of accurate real-time information as about the constantly varying spatial distribution of the suspended harmful fine particles in the atmosphere, as well as their velocity and direction.

What is claimed is:

1. A remote particle counter in a radar apparatus for remote measurement of a number and size distribution of suspended fine particles in the atmosphere comprising a control/analysis system that performs not only overall control of the system but also data measurement and analysis, a pulsed laser generator, laser beam emitting optics for transmitting a spread beam of laser light toward the atmosphere, scattered light collecting optics by which backward scattered light that occurred from fine particles upon illumination with laser light is collected on a detector, and a high-sensitivity two-dimensional photo detector having a fast gating capability, wherein a target area in which a population of fine particles suspended over a certain area of the atmosphere at a certain altitude is illuminated with pulsed laser light of a wide beam spread which has been emitted from the laser generator controlled by the control/analysis system and which has passed through the laser beam emitting optics, and backward scattered light from the distributed atmosphere fine particles is collected by the scattered light collecting optics to be picked up by the high-sensitivity two-dimensional photo detector, which is controlled by the control/analysis system to measure the number and size distribution of the fine particles; and wherein by controlling the direction of laser emission and the delay time from laser emission of the fast gating of the high-sensitivity two-dimensional photo detector, the number and size distribution of fine particles suspended in a cylindrical space of the atmosphere which is away from the position of laser emission is obtained.

2. The remote particle counter according to claim 1, wherein the image of the scattered light from the individual faraway fine particles in the atmosphere as measured with the high-sensitivity two-dimensional photo detector having the fast gating capability looks like either a dense or sparse cloud of spots, which are analyzed to determine the number and size distribution of the fine particles within the limited space of the atmosphere, the latter being determined by the brightness or intensity of the spots.

3. The remote particle counter according to claim 1, wherein the delay time in shutter closure by the fast gating capability of the high-sensitivity two-dimensional photo detector and the direction of laser emission are varied and controlled continuously and independently so as to provide information about the three-dimensional spatial distribution over a broad range of the number and size distribution of the fine particles in the atmosphere.

4. The remote particle counter according to claim 1, wherein the temporal changes in the spatial distribution of the number and size distribution of the fine particles in the atmosphere as obtained by controlling the delay time and the direction of laser emission are captured and analyzed to obtain information about the wind velocity and direction of the atmosphere.

* * * * *